(12) United States Patent
Riina et al.

(10) Patent No.: US 9,532,889 B2
(45) Date of Patent: Jan. 3, 2017

(54) Y-LOCK TRACHEAL STENT SYSTEM AND METHOD OF USE

(71) Applicants: Howard Riina, Scarsdale, NY (US); Robert Ward, New York, NY (US); Jonathan Tippett, Vancouver (CA); Fedja Mulabdic, North Vancouver (CA)

(72) Inventors: Howard Riina, Scarsdale, NY (US); Robert Ward, New York, NY (US); Jonathan Tippett, Vancouver (CA); Fedja Mulabdic, North Vancouver (CA)

(73) Assignee: NEW YORK UNIVERSITY, New York, NY (US)

( * ) Notice: Subject to any disclaimer, the term of this patent is extended or adjusted under 35 U.S.C. 154(b) by 135 days.

(21) Appl. No.: 14/624,851

(22) Filed: Feb. 18, 2015

(65) Prior Publication Data
US 2015/0230948 A1    Aug. 20, 2015

Related U.S. Application Data

(60) Provisional application No. 61/941,589, filed on Feb. 19, 2014, provisional application No. 62/016,252, filed on Jun. 24, 2014.

(51) Int. Cl.
| A61F 2/82 | (2013.01) |
| A61F 2/95 | (2013.01) |
| A61F 2/844 | (2013.01) |
| A61F 2/04 | (2013.01) |
| A61F 2/966 | (2013.01) |

(52) U.S. Cl.
CPC . *A61F 2/82* (2013.01); *A61F 2/04* (2013.01); *A61F 2/844* (2013.01); *A61F 2/95* (2013.01); *A61F 2002/046* (2013.01); *A61F 2002/9665* (2013.01); *A61F 2210/0014* (2013.01); *A61F 2310/00023* (2013.01)

(58) Field of Classification Search
CPC ...... A61F 2/23; A61F 2/203; A61F 2002/046; A61F 2/2418; A61F 2/89; A61F 2/825
See application file for complete search history.

(56) References Cited

FOREIGN PATENT DOCUMENTS

WO    WO 2012082791 A2 * 6/2012 ............. A61F 5/556

* cited by examiner

*Primary Examiner* — Thomas J Sweet
*Assistant Examiner* — Daniel Bissing
(74) *Attorney, Agent, or Firm* — Withers Bergman LLP (57) ABSTRACT

A Y-Lock tracheal stent system consisting of a stent device, for emplacement in the larynx, and a stent delivery system. A method for employing the stent delivery system to emplace the stent device.

8 Claims, 6 Drawing Sheets

Y-LOCK TRACHEAL STENT SYSTEM AND METHOD OF USE

PRIORITY

This non provisional patent application claims the benefit of priority from U.S. Provisional Patent Application 61/941,589, filed 19 Feb. 2014, and U.S. Provisional Patent Application No. 62/016,252, filed 24 Jun. 2014, the contents of which are hereby incorporated by reference herein in their entirety.

BACKGROUND

The larynx is an organ located in the human neck between the pharynx and the trachea. Nine cartilages make up the larynx including three single cartilages (epiglottic, thyroid and cricoid) and three paired cartilages (arytenoid, corniculate, and cuneiform). The larynx is further comprised of two flexible vocal folds that serve as the valve controlling the flow of air through the larynx for phonation or preventing the passage of solids and liquids to the trachea. The vocal folds are supported by the arytenoid cartilages. Muscles attached to the arytenoid cartilages control the degree of opening of the folds. Vocal fold length and tension can be controlled by rocking the thyroid cartilage forward and backward on the cricoid cartilage, by manipulating the tension of the muscles within the vocal folds, and by moving the arytenoids forward or backward.

Externally induced physical trauma can cause deformation of the structure of the larynx thereby interfering with the proper functioning of the vocal folds. There are also, for example, several disorders that can cause functioning of the vocal folds to degrade including:

Presbylarynx is a condition in which age-related atrophy of the soft tissues of the larynx results in weak voice and restricted vocal range and stamina.

Vocal cord paresis is weakness of one or both vocal folds that can greatly impact daily life.

Vocal cord plegia in which all voluntary movement of the vocal folds is lost.

Idiopathic laryngeal spasm.

Laryngomalacia that is a very common condition of infancy, in which the soft, immature cartilage of the upper larynx collapses inward during inhalation, causing airway obstruction.

Post radiation nerve and muscle injury.

Post-surgical nerve and muscle injury.

In some cases, the treatment of these conditions involves the placement of a mechanical support mechanism or stent to restore the required geometry to the structure of the larynx. For these modalities, the anchoring of the stent must be sufficiently secure to insure that the desired abduction force is stably applied. Some desirable features for such a stent include:

Biologically non-reactive—The stent should be of a construction and fabricated of materials that are biologically non-reactive.

Endoscopic Placement—The stent should be capable of endoscopic delivery with minimum potential for damaging to the contacted tissues.

Conformal—The stent should readily conform to the dimensions of the installation site and exert the required level of support force.

Atraumic—The stent should not migrate below nor cause degradation to the surface of the contacting tissue.

Repositionable—The stent should be repositionable by endoscopic methods even after an extended time period.

Removable—The stent should be endoscopically removable with minimal tissue damage.

BRIEF SUMMARY OF THE INVENTION

In non-limiting embodiments there is presented a medical stent with an anchor portion comprising a plurality of resilient parallel anchor loops that define a cylindrical surface. The resilient anchor loops may be joined at corresponding points on their perimeters by at least two linear spines. The linear spines may be parallel to axis of the cylindrical surface and at least one of the linear spines may comprise at least one deployment connector. The medical stent may also include a Y-crown portion comprising a resilient Y-crown loop flexibly joined at one point on its perimeter to one of the linear spines in proximity to one of the resilient anchor loops. The Y-crown portion of the medical device may further comprise one or more contact pads located on perimeter of the resilient Y-crown loop. The Y-crown loop may be oriented non-parallel to the anchor loops.

The medical stent, further, may be operatively configured so that a first force applied parallel to one of the linear spines in opposition to a second force applied parallel to a second of the linear spines causes an anchor portion cross sectional area, as projected on a plane perpendicular to the axis of the cylindrical surface, of the resilient anchor loops to decrease.

The medical stent, may also be operatively configured so that a first force applied parallel to one point on the perimeter of the resilient Y-crown loop in opposition to a second force applied parallel to a second point on the perimeter of the resilient Y-crown loop causes a Y-crown portion cross sectional area, as projected on a plane perpendicular to the axis of the cylindrical surface, of the resilient Y-crown loop to decrease.

The medical stent may further comprise a delivery portion that comprises a delivery wire assembly and a delivery cup assembly. The delivery wire assembly may comprise a cylindrical tube containing a movable coaxial delivery wire, an attachment coupling located at a distal end of the delivery wire configured to engage the deployment connection positioned at the linear spline. Alternatively, the delivery wire assembly may comprise a deployment connection positioned on a portion of the anchor loop. The delivery wire assembly may further comprise an activation device, located at the proximal end of the delivery wire, that is connected by the delivery wire to the attachment coupling and operatively configured to actuate the attachment coupling in response to an applied external force. The delivery cup assembly may comprise a cylindrical hollow tube defining a delivery cup cross sectional area smaller than the anchor portion cross sectional area. The delivery cup assembly may further comprise an elongated shaft that, at its distal end, is laterally connected to a proximal end of the cylindrical hollow tube and, at its proximal end, is attached to a handle.

The medical stent may be formed of nickel-titanium (i.e. nitinol) or other suitable materials and may be self-expanding.

The outer surfaces of the anchor portion and the Y-crown portion of the medical device may be textured.

DESCRIPTION OF FIGURES

The present invention will be more fully understood from the accompanying drawings of various embodiments of the invention. The drawings, however, should not be taken to limit the invention to the specific embodiments but are for explanation and understanding only.

DETAILED DESCRIPTION OF THE NON-LIMITING EMBODIMENTS

Figures 1, 2:
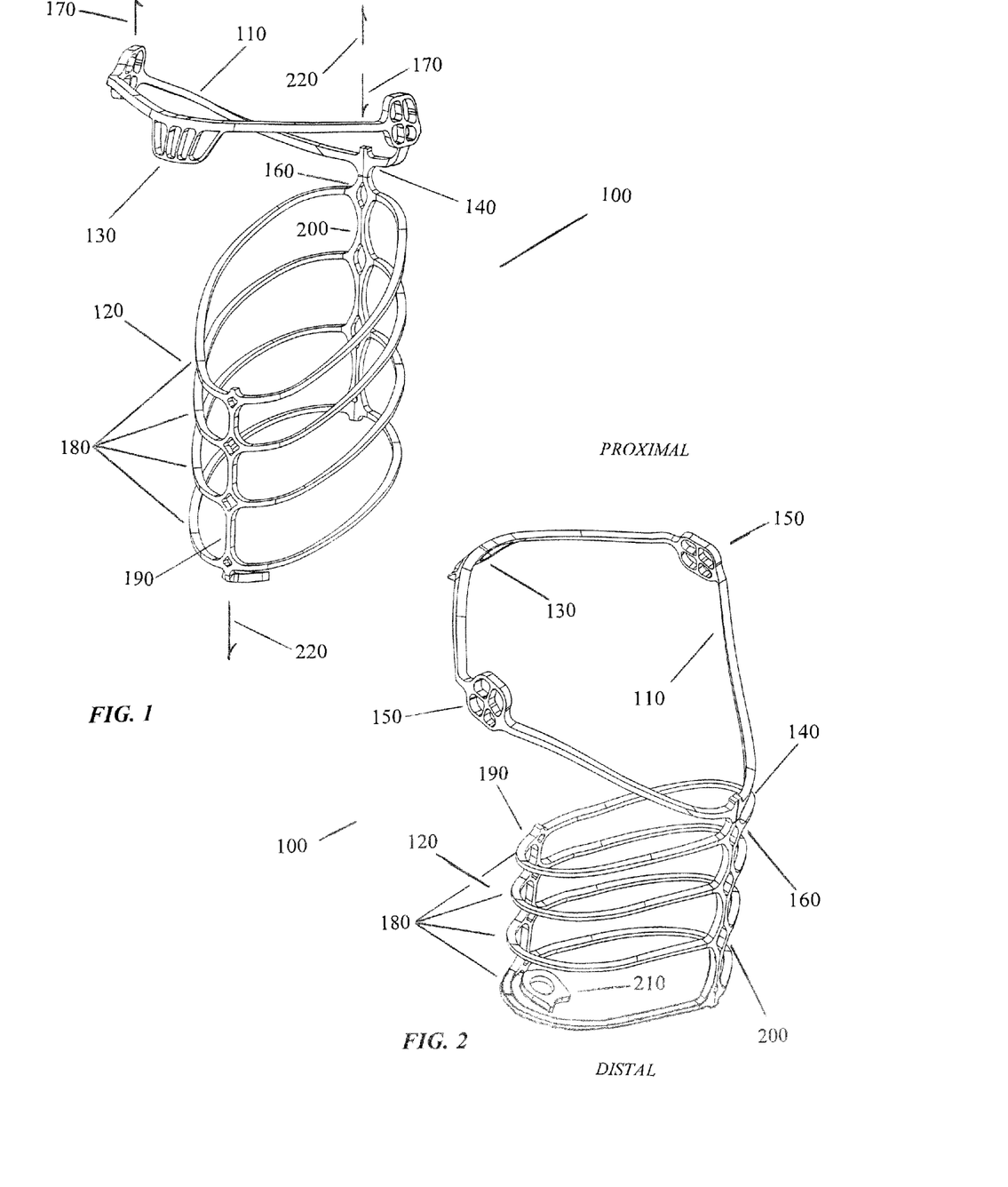
FIG. 1 is an anterior proximal perspective view of the Y-Lock stent.
FIG. 2 is a posterior proximal perspective view of the Y-Lock stent.

A first non-limiting embodiment of a stent 100, suitable for arytenoid abduction, is presented in the anterior perspective in FIG. 1 and the posterior perspective in FIG. 2. While the description pertains to the treatment of the arytenoid cartilages, other non-limiting embodiments of the invention, suitable for treatment of other pathologies is envisioned, and will be obvious to those of typical expertise in the field.

The stent 100 is comprised of a Y-lock crown 110 that is resiliently connected to an anchor 120. The Y-lock crown 110 is a resilient loop sized to diagonally set within the larynx immediately above the trachea. When emplaced, the proximal extremity of the Y-lock crown 110, comprising a center contact pad 130, may be deployed to exert an upward force under the apex of the vocal folds as a result of its resiliency. The magnitude of the upward force is determined, in part, by the mechanical properties of the stent and placement of the distal extremity 140 of the Y-lock crown 110 with respect to the center contact pad 130. The outer periphery of the Y-lock crown 110 may also incorporate pads 150 configured to control contact properties such as contact pressure loading and contact friction. The distal extremity 140 of the Y-lock crown 110 is connected to the proximal extremity 160 of the anchor.

As envisioned, an assortment of stents of different geometries and resiliencies would be available for selection based on the specific application. The resiliency properties may be determined by the mechanical properties of the fabrication material and its dimensions (i.e. thickness, geometry, etc.).

The Y-lock crown 110 may be configured so that the application of opposing axial forces 170 applied to the proximal and distal points of the resilient loop 110 cause the cross sectional area to decrease. This feature may be used to advantage during placement wherein the stent may be inserted through narrow portions of the larynx.

The anchor 120, in this non-limiting embodiment, comprises four resilient loops 180 each of which is connected, at corresponding points, to anterior 190 and posterior 200 linear spines. The anterior linear spine 190 may comprise a deployment connector 210 at its distal extremity. In other non-limiting embodiments, additional deployment connectors (not shown) may be located at one or more of the extremities of the anterior 190 and posterior 200 linear spines. In addition, other non-limiting embodiments comprising a greater or lesser number of resilient loops 180 is also envisioned.

Each of the resilient loops 180, at rest, is sized to have a cross sectional area that, when projected on a plane perpendicular to the axis of the trachea, is greater than that of the trachea. Deployment of the anchor 120 may be facilitated by reducing the loop's 180 cross sectional area. Once emplaced in the trachea, the anchor's 120 resilient properties cause the cross sectional dimensions of the anchor loops 180 to expand until conformal contact with the tracheal walls is established. This expansion anchors the stent with respect to the trachea. The outer surfaces of the anchor 120 may include contact pads (not shown) and/or be treated to enhance the frictional characteristics.

For emplacement in the trachea, the application of opposing forces 220 to the distal end of the anterior linear spine 190 and the proximal end of the posterior linear spine 200 cause the resilient loops 180 to stretch thereby reducing their cross sectional area permitting insertion into the trachea.

Figures 12, 13:
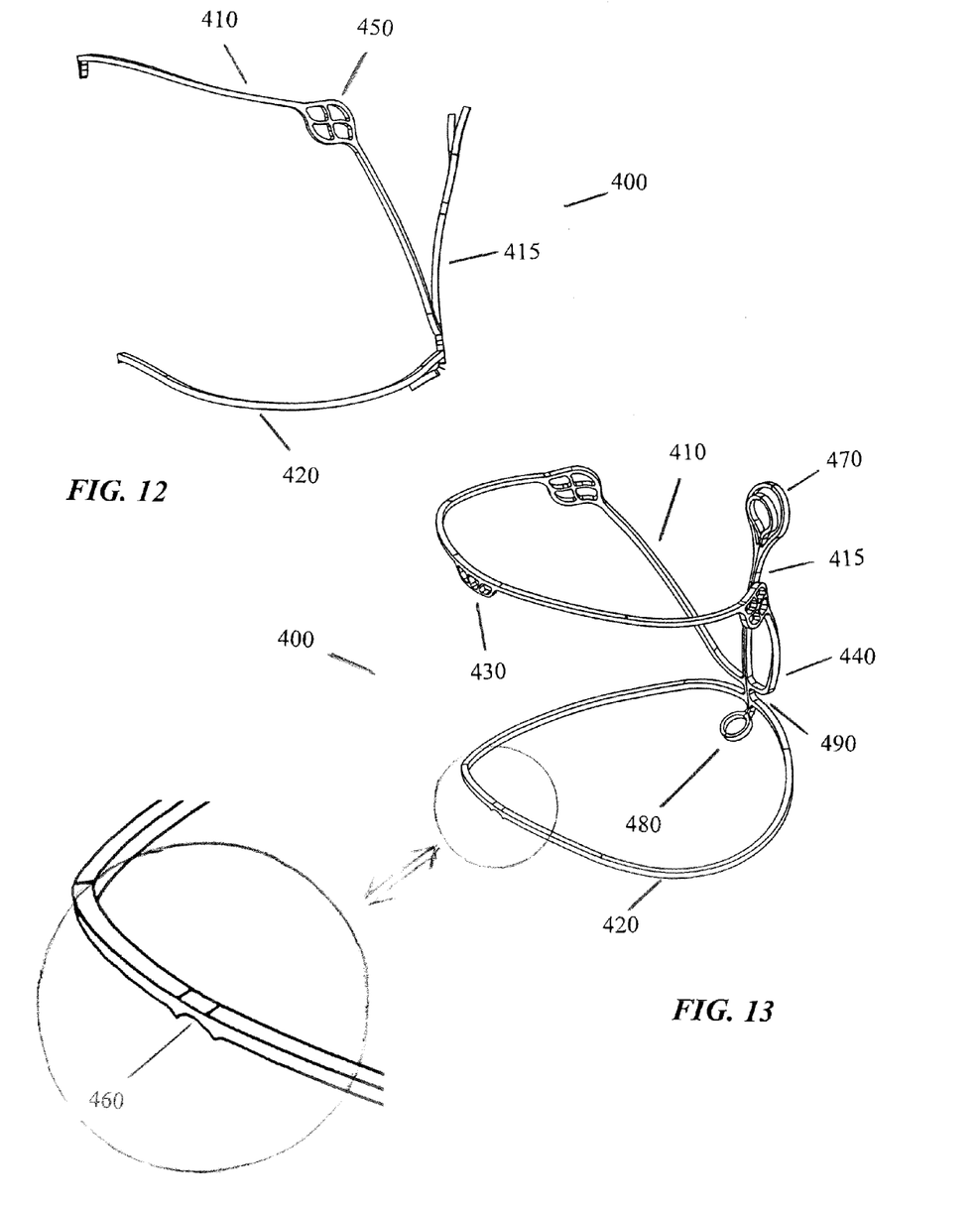
FIG. 12 is a side view of a second non-limiting embodiment of the Y-Lock stent.
FIG. 13 is an anterior proximal perspective view of a second non-limiting embodiment of the Y-Lock stent.

In a second non-limiting embodiment, a stent 400 is presented in FIGS. 12 and 13 comprises a single resilient anchor loop 420, a cantilever tail 415, and a Y-lock crown 410. This stent 400 is suitable for being positioned in entirely within the subglottis.

In this second non-limiting embodiment, the single resilient anchor loop 420, when physically unconstrained, is sized to have a cross sectional area that, when projected on a plane perpendicular to the axis of the subglottis, is greater than that of the subglottis. Deployment of the anchor 420 may be facilitated by reducing the loop's 420 cross sectional area. Once emplaced, the anchor's 420 resilient properties cause the cross sectional dimensions of the anchor loop 420 to expand until conformal contact with the subglottal walls is established, thereby anchoring the stent. The outer surfaces of the anchor loop 420 may include contact pads (not shown) and/or be treated to enhance the frictional characteristics. The single anchor loop further comprises a downward facing anchor loop notch or saddle 460 located at the anterior portion of the anchor loop 420. The anchor loop notch 460 is configured to restrict slippage of tools employed during maipulation of the anchor loop 420.

In this second non-limiting embodiment, a cantilever tail 415 is attached vertically to the posterior portion of the single resilient anchor loop, diametrically opposite to the anchor loop notch 460. The cantilever tail 415 is vertically oriented approximately perpendicular to the plane of the anchor loop 420. The cantilever tail 415 extends vertically upwards and is terminated by a tail tab 470. The downward extension of the cantilever tail 415 is terminated by an attachment tab 480.

In a third non-limiting embodiment, the anchor loop notch 460 may be used to attach the device to an alternate delivery system 300A.

The Y-lock crown 410 is a resilient crown loop sized to diagonally set within the subglottis. When emplaced, the proximal extremity of the Y-lock crown 410, comprising a center contact pad 430, may be deployed to exert an upward force under the apex of the vocal folds as a result of its resiliency. The magnitude of the upward force is determined, in part, by the mechanical properties of the stent and placement of the distal extremity 440 of the Y-lock crown 410 with respect to the center contact pad 430. The crown loop 410 is fastened, at a point opposite the center contact pad 430, to the cantilever tail 415 in proximity to the anchor loop attachment point 490. The outer periphery of the crown loop 410 may also incorporate pads 450 configured to control contact properties such as contact pressure loading and contact friction.

Figure 3:
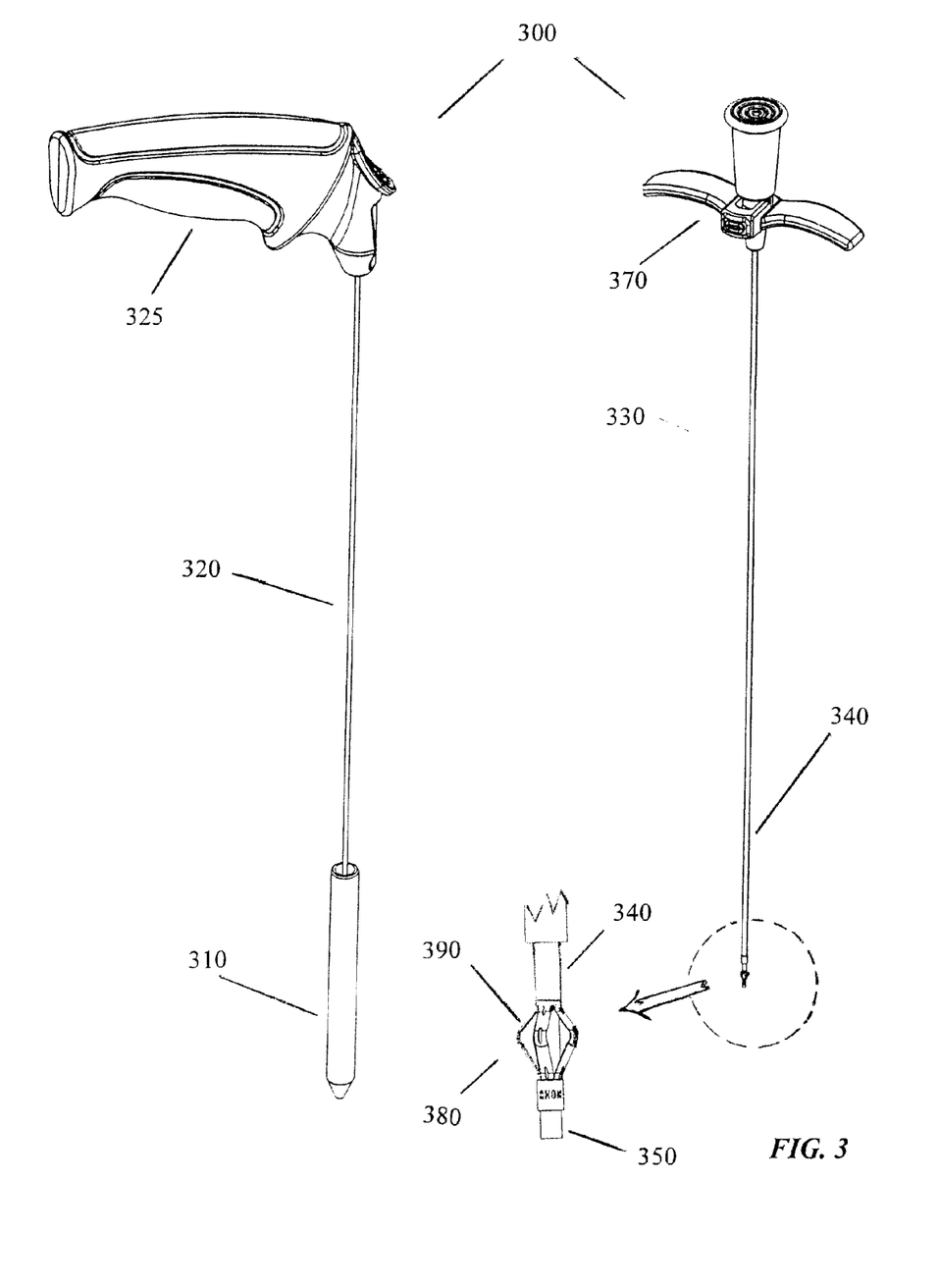
FIG. 3 is an illustration of the delivery system comprising the delivery wire component and the cylindrical cup.

The emplacement of the stent 100 into the trachea may be facilitated by the use of a delivery system 300. In an non-limiting embodiment, as shown in FIG. 3, the delivery system 300 comprises a cylindrical tube or cup 310 that is open at the proximal end. The cross sectional area of the cylindrical cup 310 has a smaller cross section than the passageway of the larynx thereby facilitating insertion through the larynx. The proximal and distal edges of the cup 310 may be chamfered or beveled or otherwise configured to further facilitate stent insertion. The cup 310 may be equipped with an extended shaft 320 fastened parallel to the cylindrical axis of the delivery cup 310. The length of the shaft 320 is sufficient to permit the cup 310 to be inserted into the trachea. It is envisioned that an assortment of cup diameters and lengths may be available from which one of appropriate dimensions for the particular application may be selected. The proximal end of the extended shaft 320 may comprise a handle 325.

The delivery system 300 further comprises a delivery wire component 330 that may be inserted into the throat to apply force to the appropriate portions of the stent 100 during emplacement, repositioning and removal procedures. The delivery wire component 330 may comprise an elongate hollow tube 340 containing an coaxial internal drive shaft 350. The distal end of the internal drive shaft 350 may incorporate a coupler 360 that is activated by relative movement between the internal drive shaft 350 and the elongate hollow tube 340. The proximal portion of the delivery system 300 may comprise an activation mechanism or handle 370 that is configured to activate the coupler 360 by causing relative movement of the internal drive shaft 350 with respect to the elongate hollow tube 340.

Figure 4:
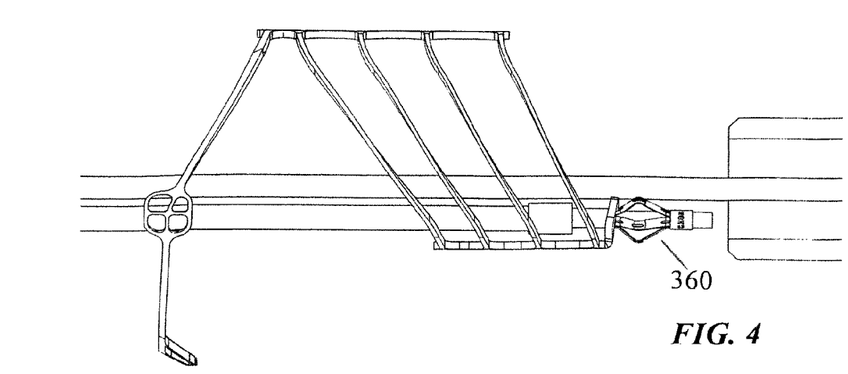
FIG. 4 is a close-up view of the stent's deployment connector engaging the coupler.
Figure 5:
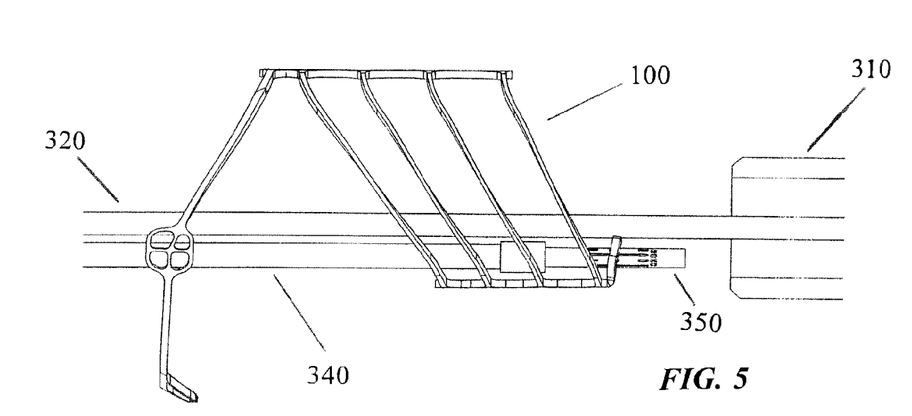
FIG. 5 is a close-up view showing the coupler passing through the stent's deployment connector.
Figure 6:
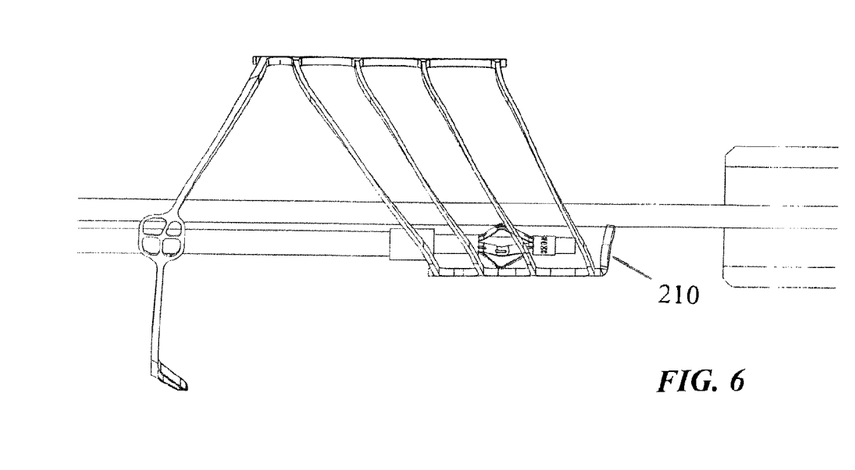
FIG. 6 is a close-up view showing the coupler withdrawn from the stent's deployment connector.

The coupler 360 may comprise a cylindrical cage or umbrella 380 having a distal end affixed to the distal end of the internal drive shaft 350 and a proximal end affixed to the distal end of the elongate hollow tube 340. The cylindrical cage 380 may comprise a plurality of flexible linear ribs 390, parallel to the axis of the internal drive shaft 350, arranged around the circumference of the internal drive shaft 350. As illustrated in FIGS. 4 and 6, differential linear movement of the internal drive shaft 350 with respect to the elongate hollow tube 340 causes the flexible linear ribs 390 of the cylindrical cage 380 to expand thereby increasing the outer diameter of the cage 380. In its expanded state, the coupler 360 will not pass through the deployment connector 210 and may be used to apply lateral force, required for stent deployment or removal. A manually activated mechanism 370 may be employed to supply differential linear movement necessary to expand the cage 380. In its unexpanded state, as shown in FIG. 5, the tip of the internal drive shaft 350 incorporating the coupler 360 may be pass through the deployment connector 210.

Figures 14, 15, 16:
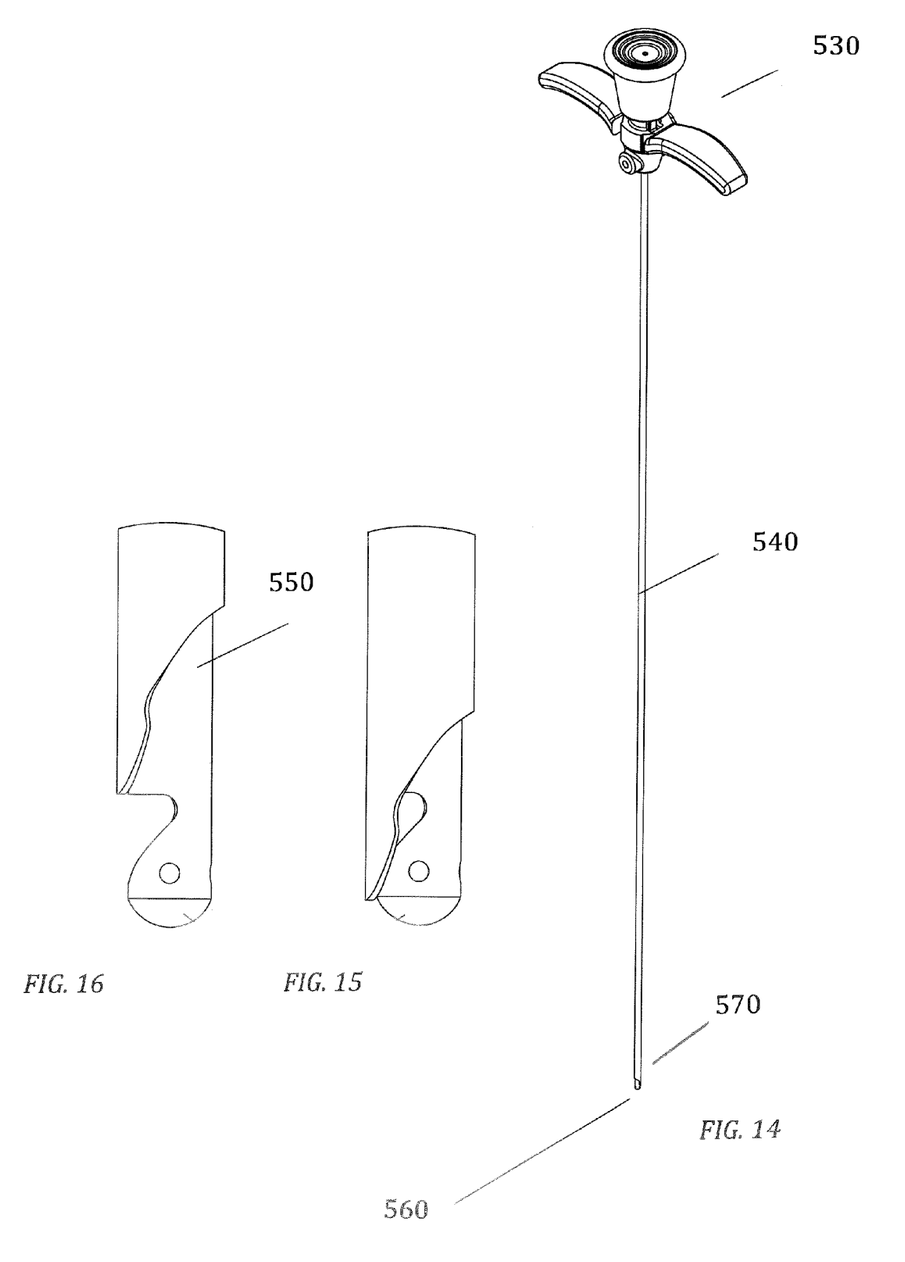
FIG. 14 is an illustration of a second non-limiting embodiment of a stent delivery system.
FIG. 15 is an illustration of the coupler of a stent delivery system in its closed state.
FIG. 16 is an illustration of the coupler of a stent delivery system in its open state.

In a second non-limiting embodiment of the delivery system, as shown in FIG. 14, the coupler 560 comprises a notch or a gate opening at the distal end of the inner drive shaft 550 and a locking sleeve 570 at distal end of the cylindrical elongated outer tube 540. Differential linear movement of the internal drive shaft 550 with respect to the elongate hollow tube 540 causes the inner drive shaft and locking sleeve to advance forward and expose the gate opening. In the closed state, as shown in FIG. 15, the anchor loop notch will not pass through the gate opening and may be used to apply lateral force required for stent deployment or removal. In the open state, as shown in FIG. 16, the gate opening is exposed and the device is released from the anchor loop notch 460. In the second non-limiting embodiment, the delivery wire assembly may further be utilized to assist in the reposition of the Y-Lock device. The delivery wire assembly gate mechanism may be secured to any portion of the Y-Lock device that can then be reposition by applying lateral force. In a second non-limiting embodiment, the delivery wire assembly nose is smoothly formed to minimize the possibility of damage to the surrounding tissue.

The delivery system may further comprise a 90° hook instrument to assist in placement or removal of the stent. The 90° hook instrument may comprise an elongate shaft with a 90° bend at its distal extremity. The end of the perpendicular portion of the hook instrument is smoothly formed to minimize the possibility of damage to the surrounding tissue.

In preparation for emplacement, the stent 100 may be inserted into the delivery cup 310 by inwardly pulling the proximal extremity of the stent 100 into the delivery cup 310. The inward pulling force may be exerted by the delivery wire component 330 coupled to the proximal deployment connector 210. The stent's 100 flexibility allows it to deform as it is inserted into the delivery cup 310. The cup 310 is of a length that can substantially contain the stent 100 in its deformed state.

Figure 7:
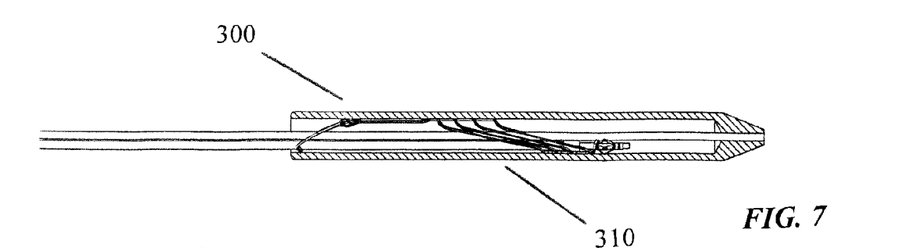
FIGS. 7 through 11 are a sequence of views of the stent being withdrawn from the delivery system cup.
Figure 8:
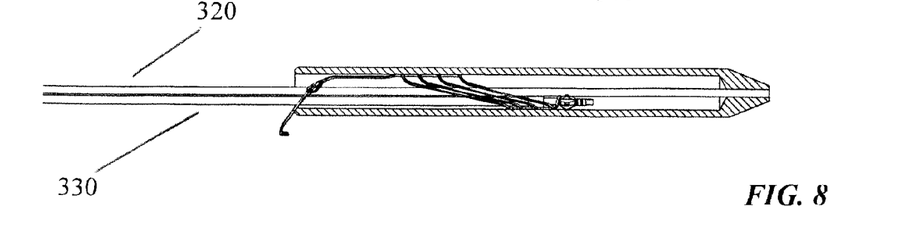
Figure 9:
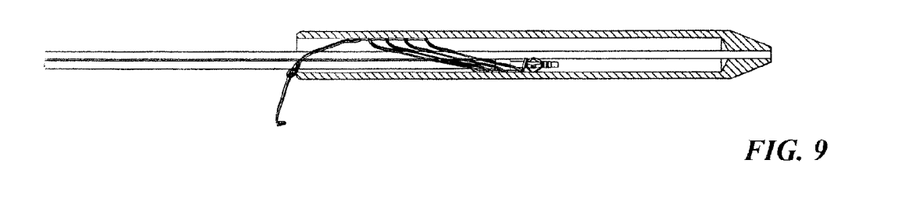
Figure 10:
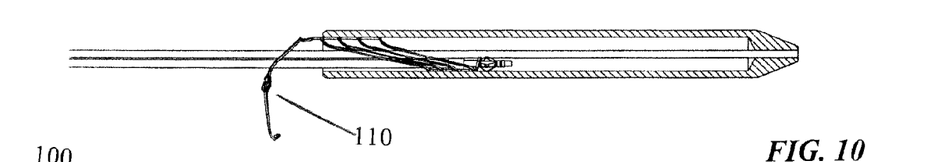
Figure 11:
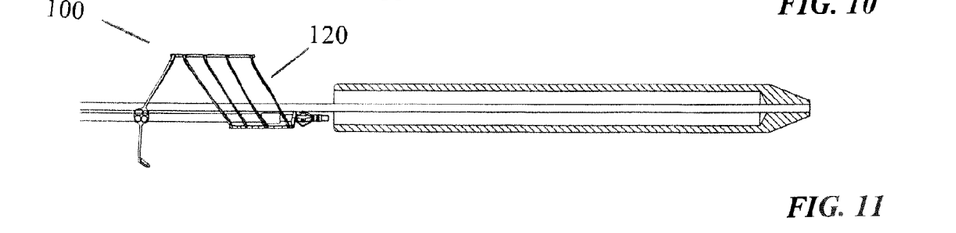

Emplacement of the stent 100 is accomplished, as shown in FIGS. 7, 8, 9, 10, and 11, by inserting the delivery cup 310 into the larynx and withdrawing the stem 100 from the delivery cup 310. The withdrawing force may be exerted by the delivery wire component 330 coupled to the proximal deployment connector 210. In FIG. 7, the stent 100 is fully contained within the delivery cup 310. In this configuration, the stent 100 may be transported to the emplacement location within the larynx. In this view, the delivery wire component 330 is attached to the stent 100 at the deployment connector 210. FIGS. 8 and 9 show the stent 100 being deployed from the delivery cup 310 by application of a withdrawal force by means of the delivery wire component. FIG. 10 shows the Y-lock crown 110 fully deployed. In this configuration, the forward pad 130 may be positioned to exert an upward force under the apex of the vocal chords. Having positioned the Y-lock crown 110, continued application of the withdrawal force, as shown in FIG. 11, causes the anchor 120 to deploy from the cup 310. As the stent 100 exits the delivery cup 310, its resiliency causes it to return to its unconstrained geometry. The delivery wire component 330 may be used to deploy the stent 100 and to facilitate adjustment of the its placement. After emplacement of the stent 100, the delivery cup 310 and delivery wire component 330 may be withdrawn through opening formed by the deployed stent 100.

Subsequently, if repositioning or removal from the larynx is necessary, the stent 100 may be re-sheathed in the delivery cup 310 with the aid of the delivery wire component 330.

First Exemplary Non-Limiting Procedure for Deploying and Retrieving Stent [Tracheal Device]

An exemplary procedure for deploying the stent in the larynx comprises the following sequence of steps:

D1-1. Inserting the delivery system 300 containing the stent 100 into the trachea.

D1-2. Placing the center contact pad 130 of the Y-crown 110 under the apex of the vocal folds.

D1-3. Deploying the Y-crown 110 with the aid of the delivery wire component 330.

D1-4. Verifying the orientation and placement of the Y-crown 110 and, if necessary, re-sheathing and re-deploying.

D1-5. Deploying the anchor 120.

D1-6. Removing the delivery cup 310.

D1-7. Releasing and removing the delivery wire component 330.

D1-8. Engaging and pulling the proximal deployment connector 210 of the anterior spine 190 proximally to wedge the anterior spine 190 against the posterior spine 200.

D1-9. Engaging and pulling on the proximal deployment connector 210 of the posterior spine 200 to increase the spreading of the Y-crown pads 150 and control the amount of vocal folds abduction.

Conversely, an exemplary non-limiting procedure for retrieving the stent from the larynx comprises the following sequence of steps:

R1-1. Engaging the delivery wire component 330 with the distal deployment connector 210 on the anterior spine 190.

R1-2. Inserting the delivery cup 310 and placing it distal to the stent 100.

R1-3. Pushing on the delivery wire component 330 while simultaneously pulling on the delivery cup 310 to insert and sheath the stent 100 in the delivery cup 310.

R1-4. Withdrawing the delivery cup 310.

Second Exemplary Non-Limiting Procedure for Deploying and Retrieving Stent [Subglottic Device]

Sheathing the Device for deployment:

S2-1. Engage the attachment tab with the Delivery Wire.

S2-2. Slide the Delivery Cup through the Device.

S2-3. Feed the anchor by hand, starting with its anterior end, into the Delivery Cup.

S2-4. Place the tip of the Delivery wire into the Delivery Cup and push on the Delivery Wire to sheathe the rest of the Device.

Deployment sequence:

D2-1. Advance the Delivery Cup distal to the vocal folds.

D2-2. Begin to unsheathe the device—the Y-Crown protrudes radially away from the Delivery Cup.

D2-3. Place the anterior pad of the Y-Crown under the apex of the vocal folds.

D2-4. Continue to unsheathe the Y-Crown placing the lateral pads just under the vocal folds.

D2-5. Affirm the position of the pads by pulling on the Delivery Wire until a moderate amount of resistance is felt.

D2-6. Maintain this amount of pull on the Delivery Wire while simultaneously pushing on the Delivery Cup to completely unsheathe the Device.

Note: During the above process, the Device can be resheathed and re-deployed for as long as a part of the Anchor Loop is still in the Cup (easier if the attachment tab is still in the Cup). Once the entire Device has been completely unsheathed, it can be resheathed for removal but in this configuration (i.e. attachment tab first) it oilers less controlled unfolding of the components during deployment. It is recommended that the Device be withdrawn and resheathed for deployment (i.e. Anchor first).

D2-7. Withdraw the Delivery Cup.

D2-8. Release and withdraw the Delivery Wire—keep it straight to prevent it from jamming.

D2-9. Insert the 90° hook instrument in the Tail tab hole and tug on the tail to confirm that the pads are still against the vocal folds.

D2-10. Insert the 90° hook instrument between the Anchor and the tracheal wall.

D2-11. Slide the instrument to the anterior end of the Anchor Loop until it is engaged with the notch.

D2-12. Pull on the Anchor Loop until the notch opposes the attachment tab (on the posterior side).

D2-13. Tug on the tail one more time.

Retrieval Sequence:

R2-1. Using the 90° hook instrument, gently push on the attachment tab to slightly dislodge the Device distally until the anterior pad shows between the vocal folds.

Note: Do this step slowly in order to keep the tail in the larynx. If the tail slides into the trachea, it may be more challenging to retrieve the device without resheathing.

R2-2. Hook the exposed Y-Crown with the 90° hook instrument and slowly pull the crown through the vocal folds. The tail will emerge through the vocal folds and the rest of the device will follow. If the tail gets caught on the vocal folds, use the 90° hook instrument to navigate it through the folds.

R2-3. If the Device cannot be removed with the 90° hook instrument, follow these steps to resheathe it into the Delivery Cup:

Engage the attachment tab with the Delivery Wire.

Advance the Delivery Cup distal to the device.

Push on the Delivery Wire to insert its tip into the Delivery Cup.

Push on the Delivery Wire while simultaneously pulling on the Delivery Cup to resheathe the Device.

Withdraw the Delivery Cup.

Third Exemplary Non-Limiting Procedure for Deploying and Retrieving Stent [Subglottic Device]

Sheathing the Device for Deployment:

S2-1. Engage the attachment tab with the Delivery Wire.

S2-2. Slide the Delivery Cup through the Device.

S2-3. Feed the anchor by hand, starting with its anterior end, into the Delivery Cup.

S2-4. Place the tip of the Delivery wire into the Delivery Cup and push on the Delivery Wire to sheathe the rest of the Device.

Deployment Sequence:

D2-1. Advance the Delivery Cup distal to the vocal folds.

D2-2. Begin to unsheathe the device—the Y-Crown protrudes radially away from the Delivery Cup.

D2-3. Place the anterior pad of the Y-Crown under the apex of the vocal folds.

D2-4. Continue to unsheathe the Y-Crown placing the lateral pads just under the vocal folds.

D2-5. Affirm the position of the pads by pulling on the Delivery Wire until a moderate amount of resistance is felt.

D2-6. Maintain this amount of pull on the Delivery Wire while simultaneously pushing on the Delivery Cup to completely unsheathe the Device.

Note: During the above process, the Device can be resheathed and re-deployed for as long as a part of the Anchor Loop is still in the Cup (easier if the attachment tab is still in the Cup). Once the entire Device has been completely unsheathed, it can be resheathed for removal but in this configuration (i.e. attachment tab first) it offers less controlled unfolding of the components during deployment. It is recommended that the Device be withdrawn and resheathed for deployment (i.e. Anchor first).

D2-7. Withdraw the Delivery Cup.

D2-8. Pull on the anchor Loop until the notch opposes the attachment tab (on the posterior side).

Release and withdraw the delivery wire—keep it strait to prevent it from jamming.

D2-9. Reinsert the delivery system or insert the 90° hook instrument and connect the tail tab hole. Tug on the tail to confirm that the pads are still against the vocal folds Retrieval Sequence:

R2-1. Using the delivery wire assembly device coupler or the 90° hook instrument, gently push on the attachment tab to slightly dislodge the device distally until the anterior pad shows between the vocal folds.

Note: Do this step slowly in order to keep the tail in the larynx. If the tail slides into the trachea, it may be more challenging to retrieve the device without resheathing.

R2-2. Grab the exposed Y-Crown with the delivery wire assembly or the 90° hook instrument and slowly pull the crown through the vocal folds. The tail will emerge through the vocal folds and the rest of the device will follow. If the tail gets caught on the vocal folds, use the delivery wire assembly device grabber or the 90° hook instrument to navigate it through the folds.

R2-3. If the device cannot be removed with the delivery wire assembly device grabber or the 90° hook instrument, follow these steps to resheathe it into the delivery cup"

Withdraw the Delivery Cup.

While the invention has been described with respect to preferred non-limiting embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

We claim:

1. A medical device comprising:
   a resilient anchor loop portion comprising at least a single resilient anchor loop sized to have a cross sectional area that, when projected on a plane perpendicular to an axis of a subglottis, is greater than that of the subglottis, said anchor loop further comprises a downward facing anchor loop notch or saddle located at an anterior portion of said anchor loop;
   a cantilever tail portion comprising a cantilever tail attached vertically to a posterior portion of said single resilient anchor loop, diametrically opposite to said anchor loop notch, said cantilever tail being oriented approximately perpendicular to a plane of said anchor loop, said cantilever tail extending vertically upward and terminating in a tail tab, said cantilever tail extending downward and terminating in an attachment tab; and
   a Y-lock crown portion comprising a resilient crown loop sized to diagonally set within the subglottis comprising a center contact pad, said crown loop being fastened, at a point opposite said center contact pad, to said cantilever tail proximal to the attachment point of said anchor loop.

2. The medical device, in accordance with claim 1, wherein the device further comprises a delivery system.

3. The medical device, in accordance with claim 2, wherein said delivery system comprises a delivery wire assembly, a delivery cup assembly, and a 90° hook instrument.

4. The medical device, in accordance with claim 3, wherein said delivery wire assembly comprises:
   a cylindrical tube containing a movable coaxial delivery wire;
   an attachment coupling located at a distal end of said delivery wire configured to engage said deployment connector; and
   an activation device located at a proximal end of said delivery wire that is connected by said delivery wire to said attachment coupling and operatively configured to actuate said attachment coupling in response to an applied external force.

5. The medical device, in accordance with claim 4, wherein said delivery cup assembly comprises:
   a cylindrical hollow tube defining a delivery cup cross sectional area smaller than said anchor portion cross sectional area;
   an elongated shaft that at its distal end is laterally connected to said cylindrical hollow tube and at said elongated shaft proximal end is attached to a handle.

6. The medical device, in accordance with claim 1, wherein said Y-crown portion further comprises one or more contact pads located on perimeter of said resilient Y-crown loop.

7. The medical device, in accordance with claim 1, wherein said device is formed of nickel-titanium (i.e. nitinol) and is self-expanding.

8. The medical device, in accordance with claim 1, wherein outer surfaces of said anchor portion and said Y-crown portion are textured.

* * * * *